United States Patent [19]
Jensen

[11] Patent Number: 4,795,445
[45] Date of Patent: Jan. 3, 1989

[54] HUB CONFIGURATION

[75] Inventor: Billy M. Jensen, Sandy, Utah

[73] Assignee: Becton, Dickinson and Company, Franklin Lakes, N.J.

[21] Appl. No.: 41,011

[22] Filed: Mar. 27, 1987

[51] Int. Cl.<sup>4</sup> ............................................. A61M 5/325
[52] U.S. Cl. ........................................ 604/240; 604/243
[58] Field of Search .............................. 604/240–243, 604/263, 272

[56] References Cited

U.S. PATENT DOCUMENTS

| | | | |
|---|---|---|---|
| 3,021,942 | 2/1962 | Hamilton | 604/243 |
| 3,472,227 | 10/1969 | Burke | 604/243 |
| 3,523,532 | 8/1970 | Burke | 604/240 |
| 3,523,533 | 8/1970 | Burke | 604/240 |
| 3,756,235 | 9/1973 | Burke et al. | 604/240 |
| 4,240,425 | 12/1980 | Akhavi | 604/243 |
| 4,581,024 | 4/1986 | Swenson | 604/240 |

Primary Examiner—James C. Yeung
Attorney, Agent, or Firm—Aaron Passman

[57] ABSTRACT

This disclosure is a hub which includes a resilient means designed to engage the shank of a needle, cannula or stylet and resist axial movement therebetween while holding same therein. The configuration of the hub allows the axial relationship between the needle, cannula or stylet and the hub to be set and maintained during further assembly operations. Disclosed also is a method for assembling the needle, cannula or stylet to the specifically configured hub.

15 Claims, 3 Drawing Sheets

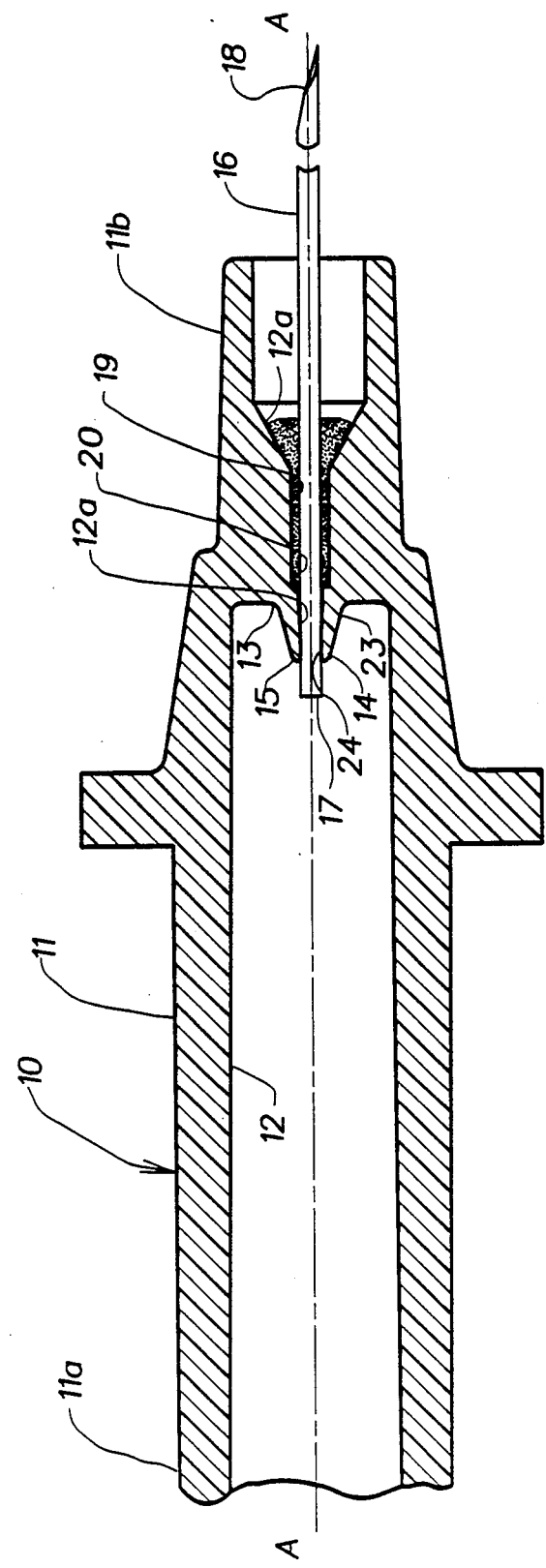

HUB CONFIGURATION

BACKGROUND OF THE INVENTION

This invention relates to an apparatus having a needle, cannula or stylet hub that holds same in position during bonding. The apparatus includes at least a deflectable member which resiliently engages the needle, cannula or stylet and holds the axial relationship between the needle, cannula or stylet and the hub while a bonding cement sets. Also disclosed is a process including the steps of resiliently engaging the needle, cannula or stylet by means of a portion on the hub during the assembly process and holding the axial position between them during a bonding operation.

In the past hubs have been arranged wherein the needle, cannula or stylet is pressed into the hub and held there by an interference fit or by an extra wedging member. These techniques cause the assembly to be largely a press fit which is subject to the tolerances in the manufacture of the outside dimension of the needle, cannula or stylet and/or the inside dimension of the hub. Such tolerances in dimensions when added to differences in material elasticity for polymeric hubs and metal needles, cannula or stylets cause uncertainty with respect to the security of the needle, cannula or stylet within the hub.

In order to overcome these concerns techniques such as welding, cementing, and the like have been added to the process to assure that the connection between the hub and the needle, cannula or stylet is secure. This is particularly important; if the needle, cannula or stylet were to be released from the hub, same could enter a human blood stream and cause series injury to a patient. A reliable bond to secure the hub and the needle, cannula or stylet is required. Accuracy of the axial location between the hub and the needle, cannula or stylet are essential. Heretofore, the length of needle, cannula or stylet extension from the hub was established by a shoulder against which the needle, cannula or stylet abutted. Tolerances could shift the axial relationship and ultimately affect the catheter axial placement relative to its needle.

SUMMARY OF DISCLOSURE

Disclosed is a hub having a hollow internal structure wherein a web portion extends inwardly and includes resilient cantilever means arranged to engage the outer diameter of a stylet, cannula, or needle. Such means are, in their relaxed position, spaced apart a distance less than the diameter of the stylet, cannula, or needle whereby insertion of the cannula, stylet, or needle will deflect the means and form a controlled friction fit. The deflection is used to hold the axial relationship of the hub to the stylet, cannula, or needle until one of them can be permanently secured by means of cement, welding, or the like. In addition such means permit the axial tolerance of the hub and needle, stylet or cannula to be overcome by an assembly technique which permits adjustment.

In the specific hub configuration the hollow central portion includes a web from which extend cantilever arms or a mouth having distal lips. Either structure will expand upon axial insertion of the stylet, cannula, or needle. This expansion is the deflection at the distal end of the cantilever and is used as a resilient spring-like arrangement which resists axial movement between the hub and the cannula, stylet, or needle during the further final assembly.

The method of axially aligning the hub and the stylet, cannula, or needle and subsequent movement along the aligned axis for engagement between the two and deflection of the cantilever means is disclosed. Once the hub and stylet have been assembled, they are held in their relative axial relationship until permanent bonding is complete.

BRIEF DESCRIPTION OF THE DRAWINGS

FIG. 3 is a side cross-sectional view of another embodiment wherein the needle is held within the hub by an extending mouth having lips which are cantilever and distal from the base or support for the mouth; these lips deflect in order to form a resilient circumferential restraining means to hold the axial relationship of the needle and hub.

DETAILED DESCRIPTION OF THE DISCLOSURE

Figure 1:
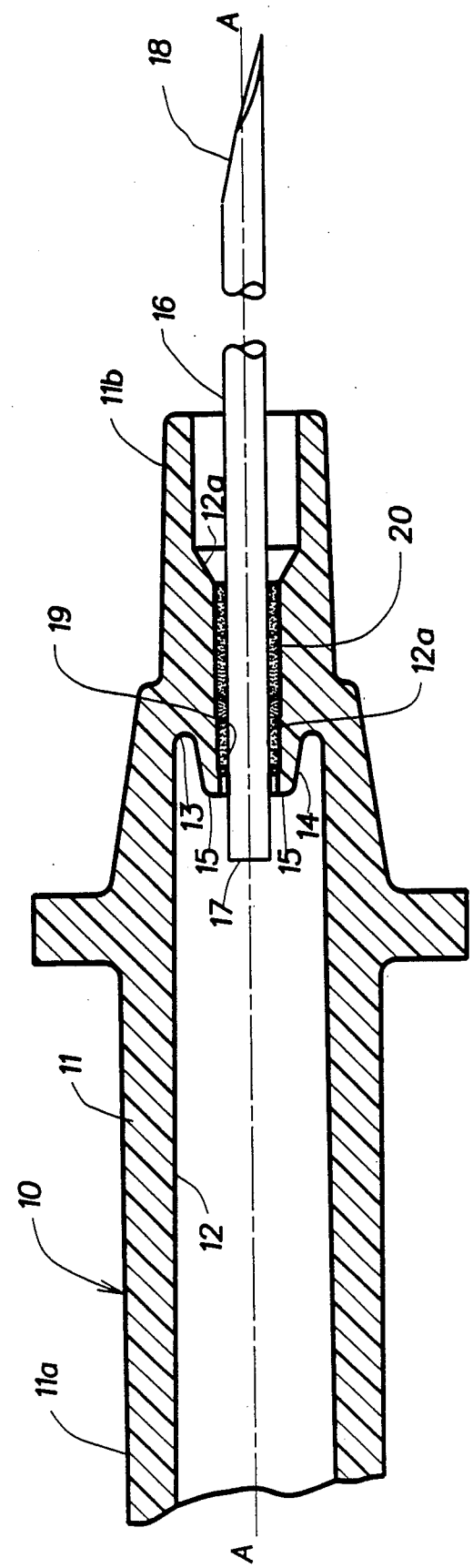
FIG. 1 is a side cross-sectional view of one embodiment of the disclosed invention showing the hub and a needle disposed within the hub and engaged thereby.

In FIG. 1 there is shown a cross-sectional view of a apparatus 10. The apparatus 10 consists of a hub or handle 11 molded from a polymeric material such as styrene, acrylics, propianate, polycarbonate, and other polymers. The hub or handle 11 includes a hollow inside 12 which forms a passage entirely through the hub or handle 11. Deposed within the center of the hollow inside 12 is a web 13 which extends inwardly from the hub or handle 11 to a central opening 12a. Web 13 is molded as part of the hub and is integral therewith. Hub or handle 11 has a handle end 11a where same is grasped during manipulation of the hub or handle 11. Passing through the central opening 12a and concentrically therewith is axis A—A shown as a broken center line in FIG. 1.

Positioned about the central opening 12a and extending from web 13 is a resilient means 14 having distal portions 15 which are furthest from web 13 and nearest handle end 11a of handle or hub 11. A needle, cannula, or stylet 16 is shown positioned within and extending through the resilient means 14 with a needle end 17 located toward the handle end 11a of hub or handle 11. The opposite end of the needle 16 has a ground bevel or point 18.

During assembly the needle 16 is axially aligned along axis A—A with its end 17 toward the handle or hub 11 whereby relative motion therebetween will move the needle end 17 and needle 16 into the hollow inside 12 of the hub or handle 11 until the end 17 has passed through central opening 12a and has been located all the way through the central opening 12a. Needle end 17 thus extends through the distal portion 15 of the resilient means 14 and is therein adjustable for length. In the past the end of the needle would seat or abut a shoulder in the hub and the extension from the hub would be a function of the needle length. With the present approach the length extended is merely a result of the position to which it is inserted. Needle extension from the hub is important since the lie distance is a function thereof. Specifically, the setback or space to the end of the catheter from the tip of the needle is critical and adjustment for needle length tolerance is important.

The natural cantilever spring-like tendency of the distal portion 15 expands same from an initial position or dimension therebetween to a deflected or greater position which is larger because same includes the deflection of the distal portion 15. The deflection expands the distal portion 15 radially outward whereby the space therethrough is now the diameter of the needle end 17 disposed therebetween.

The end of the handle or hub 11 which the needle 16 is first axially moved into is 11b and is opposite the handle end thereof 11a. Within end 11b there is a space or recess 19 which circumscribes the needle 16 and is provided for receiving cement such as epoxy to bond the needle 16 to the handle or hub 11. It can be appreciated that the resilient means 14 will hold the axial relationship between the needle 16 and the handle or hub 11 during the setting process for the cement even if heat is used. The cement is designated as 20 and is shown located within the recess or space 19 defined by the needle 16 and the handle or hub 11.

Figure 2:
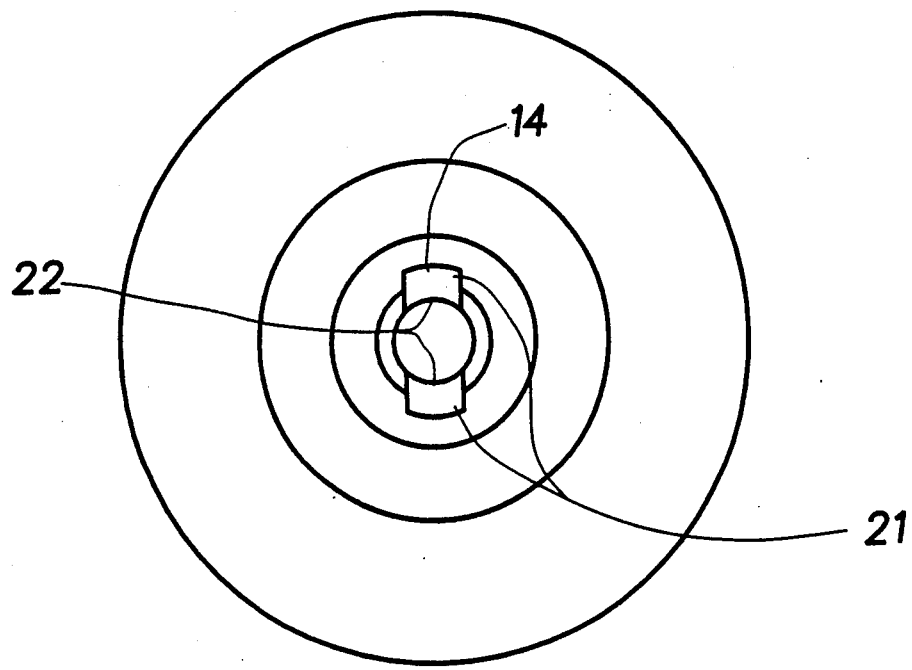
FIG. 2 is an end view looking into the hub of FIG. 1 from the end which is opposite to that from which the needle extends; shown therein are the ends of the cantilever arms which resiliently deflect to hold the needle end.

FIGS. 1 and 3 are numbered essentially the same as regards portions thereof which are identical. It should be appreciated, however, that the devices shown in FIGS. 1 and 3 are alternate embodiments of the same invention and that the differences which exist are only in the manner whereby the resilient means 14 and the distal portion 15 are specifically configured. That is to say that, in FIGS. 1 and 2 the resilient means 14 consists of a pair of oppositely opposed cantilever arms 21 having individual contact means being needle arcuate contacting surfaces 22 as best shown in FIG. 2 an end view of the device of FIG. 1. Those skilled in the art will no doubt appreciate that the cantilever arms 21 will act as extended leaf springs and deflect or move apart the distance represented by the deflection in order to engage by means of arcuate contact surfaces 22 which are shown best in FIG. 2 as a part of an arc of the circle formed by the diameter of the needle 16.

Figure 4:
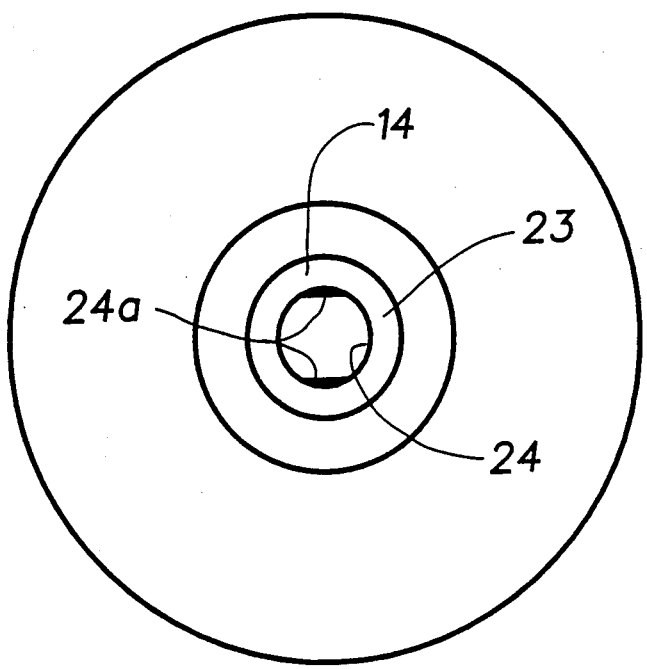
FIG. 4 is an end view looking into the hub of FIG. 3 from the end which is opposite to that from which the needle extends; shown therein is the lips which resiliently deflect to hold the needle end.

In the device shown in FIG. 3 those parts which are identical are labeled with the same figure numbers as used in FIG. 1. This alternate embodiment of apparatus 10 also has resilient means 14 and with a distal portion 15 and these are specifically an extending mouth or spout 23 which terminates in a circumscribing lip 24. This alternate arrangement is such that the mouth or spout 23 is thinned in the area of circumscribing lip 24 but has contact means being chordal flats 24a, see FIG. 4. As the needle 16 is disposed therewithin the lip 24 expands radially outward relative to axis A—A an amount equal to the deflection. The construction shown in FIGS. 3 and 4 is particularly useful for needles, cannula, or stylets which have a relatively small diameter such as those used for pediatric sizes. The arrangement of a circumscribing lip 24 and more particularly the chordal flats 24a give particularly good vise-like contact between the needle 16 diameter and the extending mouth or spout 23. Consequently, there is firm engagement which secures the axial position of the needle 16 relative to the handle or hub 11 during the cementing or bonding process.

The preferred method of assembly includes the steps of positioning the hub or handle 11 in alignment with axis A—A and the needle 16 also in alignment with axis A—A, and then moving either one or both of them along the axis A—A toward each other until they are completely engaged and the preferred length of needle extension achieved. More specifically and in connection with the preferred method, the needle 16 is inserted into the hub or handle 11 with the handle end 17 of the needle 16 first engaging the resilient means 14 and flexing same by deflecting the distal portion 15. Insertion is to a predescribed needle, cannula or stylet length without concern for tolerances because the needle, cannula or stylet can be axially inserted against the resistance of the resilient means in a controlled manner to the preferred extension length. Thereafter, the needle 16 is held in its preferred axial position relative to the handle or hub 11 during a bonding operation including the insertion of epoxy cement 20 into the space or recess 19 and the curing of same to permanently hold the needle 16 securely relative to the handle or hub 11.

While two embodiments have been shown and described with respect to the present invention, those skilled in the art will no doubt appreciate that the invention can be practiced without difficulty by changing the materials, the particular configuration of the resilient means or the steps of the process used to insert the needle into the handle or hub. With regard to the latter, insertion can be made from the other end or the option of holding the needle while moving the hub is possible. In the claims which follow the concept sought to be protected is not the particular configuration materials or order of the assembly steps, but the idea of holding one member relative to the other by resilient interconnection with an assembly technique and process that is controllable and adjustable. Subsequently the hub and needle are permanently secured to each other

What is claimed is:

1. An apparatus arranged to hold the relative coaxial relationship between a first and second member during an assembly operation while permitting controlled axial movement along the common axis of the first and second members comprising:
   a first member elongated along the axis thereof and being hollow internally;
   a web disposed within said first member and having a central opening in alignment with the axis of said first member;
   resilient cantilever means supported by said web and having a distal portion being capable of deflection in a radial direction generally normal to the axis;
   a second member which, when positioned along the common axis of said first and second members and within said central opening of said web, passes through said distal portion; and
   contact means positioned on said distal portion to frictionally engage a surface of said second member and resist axial movement of said second member relative to said first member during an assembly operation.

2. The apparatus of claim 1 wherein said first and second members are held in axial alignment relative to one another by said contact means of said distal portion preventing radial or axial movement relative to one another without application of direct force therebetween.

3. The apparatus of claim 2 wherein said first member is a polymeric molded disposable medical hub for us in controlling a needle, cannula or stylet.

4. The apparatus of claim 3 wherein said second member is hollow needle fashioned of metal and sharpened at an end to be positioned away from said hub and said contact means of said distal portion resists the change in axial relationship between said hub and needle during an assembly operation.

5. The apparatus of claim 4 wherein the assembly operation includes bonding said needle permanently to said hub.

6. The apparatus of claim 1 wherein said resilient means is composed of a pair of extending cantilever arms supported from said web about said central opening.

7. The apparatus of claim 2 wherein said contact means of said distal portion on the ends of said extending arms away from said web include radially inward portion located opposite one another in opposed vise-like relation for establishing a predefined space therebetween.

8. The apparatus of claim 7 wherein said pre-defined space is of a dimension less than the cross-sectional size of said second member whereby the resilience of said extending arms deflects said distal portion to frictionally engages and compressively grip said second member.

9. The apparatus of claim 8 wherein said distal portion is arcuate for defining a space which is generally circular.

10. The apparatus of claim 1 wherein said resilient means is shaped like an extending spout and said contact means of said distal portion is on the end of said spout away from said web and a lip positioned upon the radially inward extent said spout so as to establish a predetermined opening therewithin.

11. The apparatus of claim 10 wherein said pre-determined opening is circular in cross-section and has chordal flat across from one another to establish a space therebetween which is less than the transverse dimension of said second member which is tubular whereby the radial resilience of said spout causes said lip to engage said second member preventing movement between said members.

12. A process for assembling a first elongated hollow cylindrical member and a second cylindrical member axially and concentrically therewithin including the following steps, positioning the first member in alignment with the axis of the second member, moving the members along the common axis to one another, inserting the second member into and partially through the first member, engaging the surface of the second member with a resilient means formed within the hollow of the first member, flexing the resilient means so the second member passes into the first member, holding the second member in a pre-determined axial relation relative to the first member by the engagement of the resilient means, and bonding the first an second members permanently together.

13. The process of claim 12 wherein the bonding step includes placing a cement in a space provided between the first and second members.

14. The process of claim 12 wherein the step of flexing the resilient means includes moving a portion thereof from a first position of relaxation to a second position of deflection as a result of lodgement of the second member within the resilient means of the first member.

15. The process of claim 12 wherein the step of flexing stresses cantilever members near their extremities to form a gripping vise with a friction fit therebetween and holding the second member to the first member in a predefined axial position during bonding.

* * * * *